US00PP25409P2

(12) United States Plant Patent
Kitamura

(10) Patent No.: US PP25,409 P2
(45) Date of Patent: Apr. 7, 2015

(54) ***MANDEVILLA* PLANT NAMED 'SUNPARAKITAHO'**

(50) Latin Name: *Mandevilla hybrida*
Varietal Denomination: Sunparakitaho

(71) Applicant: Kenichi Kitamura, Shiga (JP)

(72) Inventor: Kenichi Kitamura, Shiga (JP)

(73) Assignee: Suntory Flowers Ltd., Tokyo (JP)

( * ) Notice: Subject to any disclaimer, the term of this patent is extended or adjusted under 35 U.S.C. 154(b) by 108 days.

(21) Appl. No.: 13/986,652

(22) Filed: May 21, 2013

(51) Int. Cl.
*A01H 5/00* (2006.01)

(52) U.S. Cl.
USPC ..... Plt./232

(58) Field of Classification Search
CPC ..... A01H 5/02
USPC ..... Plt./232
See application file for complete search history.

*Primary Examiner* — June Hwu
(74) *Attorney, Agent, or Firm* — C. A. Whealy

(57) ABSTRACT

A new and distinct cultivar of *Mandevilla* plant named 'Sunparakitaho', characterized by its upright and vining plant habit; vigorous growth habit; freely branching habit, dense and bushy plant form; glossy dark green-colored leaves; freely flowering habit; long flowering period; and medium-sized flowers with pale pink-colored flowers with yellow orange-colored throats.

1 Drawing Sheet

Botanical designation: *Mandevilla hybrida.*
Cultivar denomination: 'SUNPARAKITAHO'.

BACKGROUND OF THE INVENTION

The present invention relates to a new and distinct cultivar of *Mandevilla* plant, botanically known as *Mandevilla hybrida* and hereinafter referred to by the name 'Sunparakitaho'.

The new *Mandevilla* plant is a naturally-occurring branch mutation of *Mandevilla hybrida* 'Kitasun-01', not patented. The new *Mandevilla* plant was discovered and selected by the Inventor on a single flowering plant from within a population of plants of 'Kitasun-01' in a controlled greenhouse environment in Higashiomi, Shiga, Japan in February, 2011.

Asexual reproduction of the new *Mandevilla* plant by cuttings in Higashiomi, Shiga, Japan since February, 2011 has shown that the unique features of this new *Mandevilla* plant are stable and reproduced true to type in successive generations.

SUMMARY OF THE INVENTION

Plants of the new *Mandevilla* have not been observed under all possible environmental conditions and cultural practices. The phenotype may vary somewhat with variations in environmental conditions such as temperature and light intensity without, however, any variance in genotype.

The following traits have been repeatedly observed and are determined to be the unique characteristics of 'Sunparakitaho'. These characteristics in combination distinguish 'Sunparakitaho' as a new and distinct *Mandevilla* plant:

1. Upright and vining plant habit.
2. Vigorous growth habit.
3. Freely branching habit, dense and bushy plant form.
4. Glossy dark green-colored leaves.
5. Freely flowering habit.
6. Long flowering period.

7. Medium-sized flowers with pale pink-colored flowers with yellow orange-colored throats.

Plants of the new *Mandevilla* can be compared to plants of the mutation parent, 'Kitasun-01'. Plants of the new *Mandevilla* differ primarily from plants of 'Kitasun-01' in flower color as plants of 'Kitasun-01' had darker pink-colored flowers.

Plants of the new *Mandevilla* can be compared to plants of the *Mandevilla* 'Sunparapibra', disclosed in U.S. Plant Pat. No. 19,649. In side-by-side comparisons conducted in Higashiomi, Shiga, Japan, plants of the new *Mandevilla* differed from plants of 'Sunparapibra' in flower color the following characteristics:

1. Plants of the new *Mandevilla* had thicker stems than plants of 'Sunparapibra'.
2. Plants of the new *Mandevilla* had leaves that were obovate in shape whereas plants of 'Sunparapibra' had leaves that were elliptic in shape.
3. Plants of the new *Mandevilla* had smaller flower throats than plants of 'Sunparapibra'.
4. Plants of the new *Mandevilla* and 'Sunparapibra' differed in flower color as plants of 'Sunparapibra' had slightly darker-colored petal lobes and throats.
5. Plants of the new *Mandevilla* had shorter peduncles and pedicels than plants of 'Sunparapibra'.

BRIEF DESCRIPTION OF THE PHOTOGRAPHS

The accompanying colored photographs illustrate the overall appearance of the new *Mandevilla* plant showing the colors as true as it is reasonably possible to obtain in colored reproductions of this type. Colors in the photographs may differ slightly from the color values cited in the detailed botanical description which accurately describe the actual colors of the new *Mandevilla* plant.

The photograph at the top of the sheet comprises a side perspective view of a typical flowering plant of 'Sunparakitaho' grown in a container.

The photograph at the bottom of the sheet is a close-up view of a typical flower and flower bud of 'Sunparakitaho'.

DETAILED BOTANICAL DESCRIPTION

The aforementioned photographs and following observations, measurements and values describe plants grown during the late winter in 15-cm containers in an outdoor nursery in Higashiomi, Shiga, Japan and under cultural practices typical of commercial production. During the production of the plants, day temperatures averaged 25° C. and night temperatures averaged 15° C. Plants were six months old when the photographs and detailed description were taken. In the following description, color references are made to The Royal Horticultural Society Colour Chart, 2007 Edition, except where general terms of ordinary dictionary significance are used.

Botanical classification: *Mandevilla hybrida* 'Sunparakitaho'.

Parentage: Naturally-occurring branch mutation of *Mandevilla hybrida* 'Kitasun-01', not patented.

Propagation:

*Type*.—By vegetative cuttings.

*Time to initiate roots*.—About two weeks at 23° C. to 25° C.

*Time to produce a rooted young plant*.—About five to six weeks at 23° C. to 25° C.

*Root description*.—Fibrous; light brown in color.

*Rooting habit*.—Freely branching; medium density.

Plant description:

*Plant and growth habit*.—Upright and vining plant habit; vigorous growth habit; freely branching habit.

*Lateral branch description*.—Length: About 203 cm. Diameter: About 3.2 mm. Internode length: About 11.75 cm. Strength: Strong. Texture: Smooth, glabrous; developed, woody. Color: Close to 146A; developed, close to N199C.

Foliage description:

*Arrangement*.—Opposite, simple.

*Length*.—About 6.5 cm.

*Width*.—About 4.4 cm.

*Shape*.—Obovate.

*Apex*.—Cuspidate.

*Base*.—Rounded, cordate.

*Margin*.—Entire.

*Texture, upper and lower surfaces*.—Smooth, glabrous; glossy.

*Venation pattern*.—Pinnate, reticulate.

*Color*.—Developing leaves, upper surface: Close to 146A. Developing leaves, lower surface: Close to 146B. Fully expanded leaves, upper surface: Close to 147A; venation, close to 144B. Fully expanded leaves, lower surface: Close to 146B; venation, close to 144D.

*Petiole length*.—About 1.5 cm.

*Petiole diameter*.—About 1.4 mm.

*Petiole texture, upper and lower surfaces*.—Smooth, glabrous.

*Petiole color, upper and lower surfaces*.—Close to 144A.

Flower description:

*Flower type and habit*.—Single salverform flowers arranged in axillary racemes; flowers face upright to mostly outwardly; freely flowering habit with about two to three flowers per inflorescence and about nine inflorescences per plant.

*Natural flowering season*.—Plants begin flowering about six weeks after planting; long flowering period, plants flower continuously from early summer to late autumn in Japan.

*Flower longevity on the plant*.—About seven to ten days; flowers not persistent.

*Fragrance*.—Slightly fragrant, pleasant.

*Inflorescence height*.—About 7.1 cm.

*Inflorescence diameter*.—About 8.8 cm.

*Flowers*.—Appearance: Salverform; flared trumpet, corolla fused and five-parted; flowers roughly star-shaped. Diameter: About 7.4 cm. Depth (length): About 7.2 cm. Throat diameter: About 1.6 cm. Tube length: About 5 cm. Tube diameter, mid-section: About 1.4 cm. Tube diameter, base: About 3.8 mm.

*Flower buds*.—Height: About 7 cm. Diameter: About 1.2 cm. Shape: Lenticular. Color: Towards the base, close to 184A; mid-section, close to 62D and 142C; and towards the apex, close to 73C.

*Corolla*.—Quantity and arrangement: Five petals arranged in a single whorl and fused towards the base into an elongated tube; petals slightly imbricate towards the throat. Petal lobe length: About 3.3 cm. Petal lobe width: About 2.9 cm. Petal lobe shape: Ovate. Petal lobe apex: Acuminate. Petal lobe margin: Entire, slightly undulate. Petal lobe texture, upper and lower surfaces: Smooth, glabrous. Throat texture: Smooth, glabrous. Tube texture: Smooth, glabrous. Color: Petal lobe, when opening, upper surface: Close to 68D and 69A. Petal lobe, when opening, lower surface: Close to 69B to 69D. Petal lobe, fully opened, upper surface: Close to 69A to 69D; color becoming closer to N155A with development. Petal lobe, fully opened, lower surface: Close to 69B to 69D. Throat: Close to 16A; longitudinal lines, close to N25A to N25C. Tube: Close to 69B and 142C; towards the base, close to N34A.

*Calyx*.—Quantity and arrangement: Five sepals arranged in a single whorl fused at the base; calyx, star-shaped. Sepal length: About 8.7 mm. Sepal width: About 2.6 mm. Sepal shape: Lanceolate. Sepal apex: Acute. Sepal margin: Entire. Sepal texture, upper and lower surfaces: Smooth, glabrous. Sepal color: When developing and fully expanded, upper surface: Close to 149C; towards the apex, close to 181C. When developing and fully expanded, lower surface: Close to 149D; towards the apex, close to 181C.

*Peduncles*.—Length: About 3.8 cm. Diameter: About 1.7 mm. Texture: Smooth, glabrous. Aspect: Obliquely upright. Color: Close to 144A.

*Pedicels*.—Length: About 1.8 cm. Diameter: About 2.2 mm. Texture: Smooth, glabrous. Aspect: Obliquely upright. Color: Close to 144B to 144D.

*Reproductive organs*.—Stamens: Quantity and arrangement: Typically five; filaments fused to corolla; anthers, connivent. Anther shape: Elliptic. Anther size: About 2 mm by 9.9 mm. Anther color: Close to 18C. Pollen amount: Scarce. Pollen color: Close to 8D. Pistils: Quantity: Typically one. Pistil length:

About 2.3 cm. Style color: Close to 145D. Stigma shape: Conical. Stigma color: Close to 144D. Ovary color: Close to 144C.

*Seeds and fruits*.—Seed and fruit production have not been observed on plants of the new *Mandevilla*.

Disease & pest resistance: Plants of the new *Mandevilla* have not been noted to be resistant to pathogens and pests common to *Mandevilla* plants.

Garden performance: Plants of the new *Mandevilla* have been observed to tolerate wind, rain and temperatures ranging from about 4° C. to about 30° C.

It is claimed:

1. A new and distinct *Mandevilla* plant named 'Sunparakitaho' as illustrated and described.

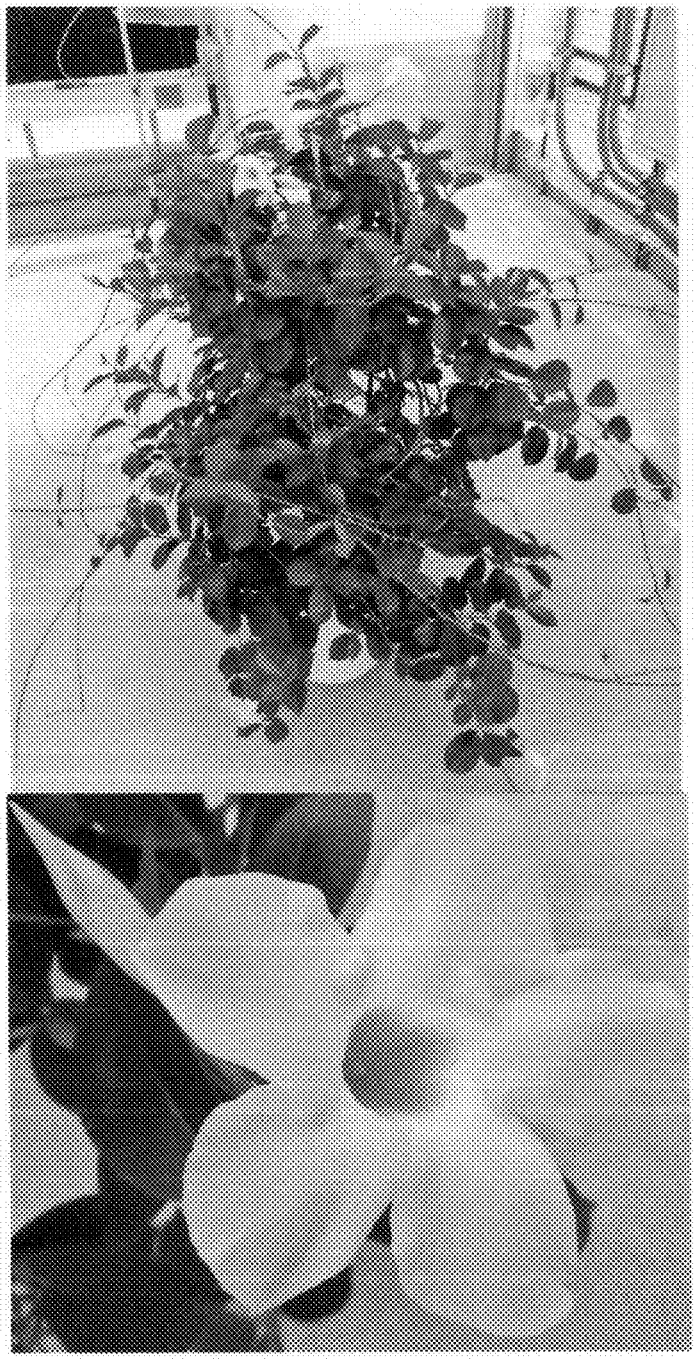

* * * * *